US006572898B2

(12) United States Patent
Nelson et al.

(10) Patent No.: US 6,572,898 B2
(45) Date of Patent: *Jun. 3, 2003

(54) ELECTROLYTE GELS FOR MAINTAINING HYDRATION AND REHYDRATION

(75) Inventors: Robert Nelson, Sugar Grove, IL (US); Mark Glowacki, Wheaton, IL (US)

(73) Assignee: PTS Labs LLC, Rosemont, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/316,500

(22) Filed: May 21, 1999

(65) Prior Publication Data

US 2002/0009502 A1 Jan. 24, 2002

(51) Int. Cl.[7] .................. A01N 59/14; A61K 47/00; A61K 9/14; A61K 9/16; A61K 9/50

(52) U.S. Cl. ............... 424/663; 424/661; 424/400; 424/439; 424/489; 424/492; 424/493; 424/494; 424/496; 424/499

(58) Field of Search ................... 426/573, 576, 426/577, 271, 103, 74, 76, 100; 514/23, 867; 424/663, 661, 400, 439, 489, 492–494, 496, 499

(56) References Cited

U.S. PATENT DOCUMENTS

| | | | |
|---|---|---|---|
| 3,956,173 A | * | 5/1976 | Towle |
| 4,307,124 A | * | 12/1981 | Moirano |
| 4,369,125 A | * | 1/1983 | Kragen et al. |
| 4,505,926 A | | 3/1985 | Newsome et al. |
| 4,539,319 A | | 9/1985 | Newsome et al. |
| 4,558,063 A | | 12/1985 | Beeley et al. |
| 4,594,195 A | | 6/1986 | Newsome et al. |
| 4,661,475 A | * | 4/1987 | Bayerlein et al. |
| 4,826,700 A | * | 5/1989 | Bayerlein et al. |
| 4,942,042 A | | 7/1990 | Bhargava et al. |
| 4,952,686 A | * | 8/1990 | Renn et al. |
| 5,038,396 A | | 8/1991 | Gjerlov |
| 5,096,894 A | | 3/1992 | Tao et al. |
| 5,192,551 A | | 3/1993 | Willoughby, Jr. et al. |
| 5,270,297 A | | 12/1993 | Paul et al. |
| 5,498,408 A | | 3/1996 | Oltra et al. |
| 5,869,458 A | | 2/1999 | Waite et al. |
| 5,869,459 A | * | 2/1999 | Waite et al. |

FOREIGN PATENT DOCUMENTS

| | | | |
|---|---|---|---|
| GB | 2219803 A | * | 12/1989 |
| JP | 04293463 | * | 10/1992 |

OTHER PUBLICATIONS

US 5,643,882, 7/1997, Waite (withdrawn)

Handlogten et al. Medicine & Science in Sports & Exercise, 31 (5), Supplement, pp S195. Meeting Info.: 46th Annual Meeting. Effect of concentrated carbohydrate–electrolyte gel on moderate–intensity intermittant exercise, Jun. 2–5, 1999.*

Andres, C. Food processing, 40 (9), p 52. Water dessert gel system is versatile, reduces cost: Gel will not melt at room temperature, 1979.*

Parents Magazine, 72 (4), p 40. Pediatrick (Brief article), Apr. 1997.*

Carpenter, C., et al. Oral–Rehydration Therapy—The Role of Polymeric Substrates, *New England J. Med.*, 1988, 319:1346–1348.

Lebenthal, E., et al., Corn syrup sugars: In vitro and in vivo digestibility and clinical tolerance in acute diarhhea of infancy, *J. Pediatr.*, 1983, 103:29–34.

Mahalanabis, D., et al., In Search of a Super Oral Rehydration Solution: Can Optimum Use of Organic Solute–Mediating Sodium Absorption Lead to the Development of an Absorption Promoting Drug?, *J. Diar. Dis. Res.*, 1983, 1:76–81.

Molla, A., et al., Rice–Powder Electrolyte Solution as Oral Therapy in Diarhhoea due to Vibrio Cholerae and *Escherichia coli*, *The Lancet*, Jun. 12, 1982, 1317–1319.

Molla, A. et al., Turning off the Diarrhea: The Role of Food and ORS, *J. Pediatr. Gastroenterology and Nutr.*, 1989, 8, 81–84.

Patra, F., et al., Is oral rice electrolyte solution superior to glucose electrolyte solution in infantile diarrhoea?, *Archives of Disease in Childhood*, 1982, 57:910–912.

Santucci, K., et al., Frozen Oral Hydration as an Alternative to Conventional Enteral Fluids, *Arch. Pediatr. Adolesc. Med.*, 1998, 152:142–146.

Sladen, G., et al., Interrelationships Between the Absorptions of Glucose, Sodium, and Water by the Normal Human Jejunum, *Clin. Sci.*, 1969, 36:119–132.

Tamer, M., et al., Successful Oral Rehydration of Mild to Moderate Dehydration: Comparison With Intravenous Therapy, *Clin. Res.*, 1983, 31:A872.

Kirk–Othmer Encyclopedia of Chemical Technology, 3rd. ed., vol. 6, p. 561–596.

* cited by examiner

Primary Examiner—Christopher R. Tate
Assistant Examiner—Michele C. Flood
(74) *Attorney, Agent, or Firm*—McDonnell Boehnen Hulbert & Berghoff

(57) ABSTRACT

A gel rehydration electrolyte composition provides a convenient and effective way of replenishing lost fluid and electrolytes. The gel rehydration electrolyte composition masks unpleasant tastes of electrolyte and is readily consumed by young children and elderly who cannot tolerate the liquid or frozen forms of electrolytes.

11 Claims, No Drawings

ELECTROLYTE GELS FOR MAINTAINING HYDRATION AND REHYDRATION

FIELD OF THE INVENTION

The invention comprises a gel electrolyte composition for the oral replacement of electrolytes in the body. In particular, the invention relates to a gel rehydration electrolyte composition. The gel rehydration electrolyte composition provides a convenient and effective vehicle for orally administering electrolytes in a way that is readily tolerated by infants, young children, and elderly patients who have difficulty tolerating liquid or frozen forms of electrolytes.

BACKGROUND OF THE INVENTION

Electrolyte solutions are conventionally used to orally replace electrolytes lost during vomiting or diarrhea or as a result of exercise. Electrolyte loss thorough diarrhea and vomiting in particular can cause a severe condition, especially in infants and young children, and may result in death. Diarrhea frequently involves colonization of the small intestine with enteropathogenic strains of *E. Coli* which produce heat stable and/or heat labile enterotoxins. Related enterotoxins are produced by other enteropthogens such as cholera, and also cause diarrhea. These enterotoxins stimulate fluid secretion in the gut lumen and cause diarrhea. Associated fluid loss may lead to death.

In cases of severe dehydration corrective parenteral (intravenous) therapy is often necessary. In cases of mild to moderate dehydration, oral rehydration solutions provide a safe and economical alternative to intravenous therapy. Oral electrolyte solutions used in oral maintenance or rehydration therapy consist of a mixture of electrolytes and a carbohydrate component such as glucose or dextrose. Examples of commercially available oral electrolyte replacement and/or maintenance solutions include Rehydroltye® and Pedialyte®, manufactured by Ross Laboratories, Columbus, Ohio, and Magonate® Liquid, manufactured by Fleming and Company, Fenton, Mo. Frozen formulations of electrolytes sold by PTS Labs have been found to be particularly advantageous in administering electrolytes to children. See, e.g., Santucci et al., Frozen Oral Hydration as an Alternative to Conventional Enteral Fluids. *Archives of Pediatrics & Adolescent Medicine*, February 1998, Vol. 152, pp. 142 to 146.

The development of oral rehydration therapy for acute diarrheal diseases of infancy and childhood has significantly reduced related morbidity and mortality, particularly in less developed countries where it constitutes the primary mode of therapy. The World Health Organization (WHO) currently recommends that oral rehydration solutions for treatment of acute diarrheal therapy contain 90 mEq sodium/liter, 20 mEq potassium/liter, 80 mEq chloride/liter, 30 mEq citrate/liter or 30 mEq bicarbonate/liter, and 110 mmol glucose/liter. Glucose is recommended as the carbohydrate component in such oral rehydration solutions. Glucose enhances the membrane transport of sodium, which in turn enables rapid uptake of water. The WHO formulation has been shown to decrease morbidity and mortality.

Substitution of other carbohydrates for glucose in WHO-type formulations has been investigated. Lebenthal et al. (*J. Pediatrics*, 1983, 103:29–34) studied the effect of three corn syrup sugars (dextrins) containing glucose polymers of varying lengths having dextrose equivalents of 10, 15 and 24 and determined they were suitable as the sole carbohydrate source in oral rehydration therapy. It has also been established that oral rehydration solutions in which rice and other food sources of starch are substituted for glucose are effective as reported by Carpenter et al. (*New England J. Med.*, 1988, 319:1346–1348). Rice-based oral rehydration solutions containing from 3 to 5% rice and having electrolyte levels corresponding to conventional WHO formulations have been found to be effective as reported by Patra et al. (*Archives of Disease in Childhood*, 1982, 57:910–912), Molla et al. (*The Lancet*, 1982, 1317–1319), and Malla et al. (*Journal of Pediatric Gastroenterology and Nutrition*, 1989, 8:81–84). U.S. Pat. No. 5,096,894 discloses an oral rehydration solution comprising a mixture of the required electrolytes and rice dextrin containing a distribution of 50–90% short chain glucose polymers consisting of 2 to 6 glucose units.

U.S. Pat. No. 5,270,297 discloses an oral rehydration solution including a blend of simple sugars, more complex carbohydrates, and minerals, particularly magnesium. Other ingredients include electrolyte ions (e.g., potassium, sodium, chloride), vitamins, anabolic nutrients, and other minerals such as calcium. The magnesium and calcium are provided in the form of amino acid chelates to facilitate rehydration and promote endurance.

U.S. Pat. Nos. 4,505,926, 4,539,319, 4,558,063 and 4,594,195 disclose various oral rehydration solutions containing pharmaceutically active ingredients (i.e., drugs) for treatment for enterotoxin induced diarrhea and prevention of death from enteropathogenic *E. coli* infection of gastrointestinal tract. Drugs incorporated into these prior art rehydration solutions include quaternary aminophenyliminoimidazolidines, 2-amino-immidazoline derivative, and 5,6,7,8-tetrahydro-naphonitrile intermediates.

U.S. Pat. No. 4,942,042 is directed to an anti-diarrhea composition comprising an absorptive component and an electrolyte/sugar component. The absorptive material is a thermally activated, finely powdered, hydrous magnesium aluminum silicate clay capable of absorbing pathogenic intestinal bacteria. The absorptive material is preferably also capable of absorbing diarrhea-associated viruses, intestinal toxins and gases. Suitable absorptive materials are clays such as Smectite ($Si_8Al_4O_{20}OH_4$). Other such clays are argillaceous clays. The electrolyte/sugar component contains a sodium salt, a potassium salt and a sugar. The composition is packaged in solid form and reconstituted by admixture with water prior to administration.

U.S. Pat. No. 5,192,551 discloses rehydration and infant nutrient formulas containing a neutral glycolipid, in particular, gangliotetracosylceramide. The glycolipid binds enteric virus, e.g., rotairuses, which are pathogenic to humans. Rotaviruses are RNA viruses known to replicate in the intestinal epithelial cells of a wide range of animal species, including humans.

Frozen electrolyte compositions and delivering systems are described in U.S. Ser. No 08/786,072, which is incorporated herein by reference.

Electrolytes generally have a disagreeable taste. As such, rehydration/electrolyte solutions are often difficult to administer, especially to young children. While unflavored or flavored oral electrolyte maintenance and replenishing solutions for infants and children are available, such as Fruit-Flavored Pedialyte® manufactured by Ross Laboratories, Columbus, Ohio, frozen electrolyte formulations (such as Revitalice® sold by PTS Labs, Lake Forest, Ill.) have been demonstrated to be better tolerated in administering electrolytes to children. However, even the frozen electrolytes are in some instances not suitable for young children or elderly patients. This invention is direct at fulfilling this need.

SUMMARY OF THE INVENTION

The invention is directed to a gel electrolyte composition for oral administration of electrolytes. More particularly, the invention is directed to a gel rehydration electrolyte composition useful in the maintenance and/or replacement of electrolytes lost through diarrhea, vomiting, during physical exercise, or through other illness. Whereas all prior art oral rehydration solutions are administered in a liquid or frozen form, the composition of the invention is designed to be served in a gel form.

Thus, in a first aspect, the invention provides a gel rehydration electrolyte composition comprising:

(a) from about 80 to about 99 percent by weight water;
(b) from about 20 to about 60 mEq of sodium per liter of water;
(c) from about 15 to about 25 mEq of potassium per liter of water;
(d) from about 25 to about 50 mEq of chloride per liter of water;
(e) from about 20 to about 50 mEq of citrate per liter of water;
(f) from about 20 to about 30 grams of carbohydrate per liter of water; and
(g) from about 2 to about 10 grams of a structuring agent per liter of water.

In another aspect, the invention provides a gel rehydration electrolyte composition comprising a structuring agent that is a combination of carrageenan and locust bean gum.

In still another aspect, the invention provides a gel rehydration electrolyte composition that is a gel at room temperature, i.e. not frozen.

In a further aspect, the invention provides a dry powder which upon the addition of an amount of water provides a gel rehydration electrolyte composition comprising:

(a) from about 80 to about 99 percent by weight water;
(b) from about 20 to about 60 mEq of sodium per liter of water;
(c) from about 15 to about 25 mEq of potassium per liter of water;
(d) from about 25 to about 50 mEq of chloride per liter of water;
(e) from about 20 to about 50 mEq of citrate per liter of water;
(f) from about 20 to about 30 grams of carbohydrate per liter of water; and
(g) from about 2 to about 10 grams of a structuring agent per liter of water.

In yet a further aspect, the invention provides a method of replacing lost electrolytes or preventing loss of electrolytes comprising orally administering to an individual in need thereof a gel rehydration electrolyte composition comprising:

(a) from about 80 to about 99 percent by weight water;
(b) from about 20 to about 60 mEq of sodium per liter of water;
(c) from about 15 to about 25 mEq of potassium per liter of water;
(d) from about 25 to about 50 mEq of chloride per liter of water;
(e) from about 20 to about 50 mEq of citrate per liter of water;
(f) from about 20 to about 30 grams of carbohydrate per liter of water; and
(g) from about 2 to about 10 grams of a structuring agent per liter of water.

These and other aspects of the invention will become apparent in light of the detailed description below.

DETAILED DESCRIPTION OF A PREFERRED EMBODIMENT

The gel rehydration electrolyte composition of the invention contains all necessary electrolytes and levels thereof required by the American Academy of Pediatrics for oral rehydration formulations sold in the United States. In addition to sodium ($Na^+$), potassium ($K^+$), chloride (Cl) and citrate ions, the gel rehydration electrolyte composition contains a source of carbohydrate such as glucose or dextrose to control absorption of electrolytes and contains a structuring agent to provide a gelled or thickened composition. Fruit flavoring and sweeteners designed to mask the unpleasant tastes of electrolytes are also provided in the gel rehydration electrolyte compositions of the invention. Administration in the gel form also has been discovered to lessen the offensive taste of electrolytes.

The invention provides the art with a gel rehydration electrolyte composition for replacement or prevention of electrolyte loss through oral administration. The composition comprises a structuring agent comprising a gelling and/or thickening agent such as gum or gelatin, water, carbohydrate, sodium ions, potassium ions, chloride ions, and citrate ions in concentrations effective in replacing electrolytes in dehydrated subjects.

The invention also provides a method of replacing lost electrolytes or preventing loss of electrolytes where the liquid or frozen forms of the electrolyte are not suitable. The method comprises orally administering to an individual in need thereof a gel rehydration electrolyte composition comprising a gelling or thickening agent, water, carbohydrate, sodium ions, potassium ions, chloride ions and citrate ions in concentrations used in the liquid or frozen form.

Young children on occasion either will not drink electrolyte liquids or have a propensity to bite off large chunks of ice from freezer pops. However, the gel rehydration electrolyte composition comprising necessary electrolytes can readily be administered to young children in need of such electrolytes. Elderly also have difficulty with the intake of both liquid and frozen electrolytes and benefit from the gel rehydration electrolyte composition of this invention. In either pediatric or geriatric cases, the gel rehydration electrolyte compositions offer an effective alternative to liquids or freezer pops with patients who either will not drink, have difficulty keeping ingested material down, or cannot self-administer.

When children are sick, the usual foods and liquid are frequently reduced or discontinued, often producing a loss of essential fluids and electrolytes. Vomiting and diarrhea can result in further loss of essential fluids and electrolytes. In order to forestall dehydration and prevent fluid losses before serious deficits develop, replacement therapy is often required.

The gel rehydration electrolyte composition provides, in a convenient dosage form, a balanced formula of important electrolytes for the effective maintenance and replacement of fluid deficits. This composition is especially advantageous for children to take who are unable to tolerate the liquid or frozen forms. The gel rehydration electrolyte composition of the invention is convenient, nonthreatening, painless, and easy to administer.

The gel rehydration electrolyte composition of the invention is advantageously used to supply water and electrolytes needed to the maintenance and/or replacement of mild to moderate losses of electrolytes as in diarrhea or vomiting during illnesses. Such a composition also provides a useful way of coaxing sick children or elderly such as those in a post-operative recovery period, into taking necessary replenishing fluids.

In addition to being a useful therapeutic agent, the gel rehydration electrolyte composition of the invention is a particularly useful prophylactically. Ingestion of the gel rehydration electrolyte composition helps to maintain proper electrolyte balance and to avoid dehydration.

The gel rehydration electrolyte composition of the invention is made by first preparing a solution of potassium, sodium, chloride and a base in water. Suitable bases include acetate, lactate, citrate and/or bicarbonate. Sodium chloride, potassium citrate, sodium citrate, and potassium chloride are suitable sources of electrolytes. Citric acid may be also used. For the prevention of dehydration or maintenance of hydration, sodium ion may be added at a concentration of 20–100 mEq/L, and typically a level of from 40–60 mEq/L is sufficient. Preferred potassium levels are from 15–30 mEq/L, with a broad range of 10–100 mEq/L being operable. The chloride anion is preferably added at 30–80 mEq/L, with a broad range of 25–100 mEq/L being operable. The base, which is selected from the group consisting of acetate, lactate, citrate or bicarbonate, is preferably added to a range of 25–40 mEq/L, with broad range of 20–50 mEq/L being operable.

A structuring agent is then added to the solution of potassium, sodium, chloride and a base in water. As used herein, the term structuring agent means any gelling or thickening agent that can be combined with other necessary ingredients to provide a gel rehydration electrolyte composition having a preferred product consistency at room temperature. As used herein, the term preferred product consistency at room temperature is defined as having a gel strength in the range of from about 20 to about 1000 grams per $cm^2$, and preferably from about 100 to about 200 grams per $cm^2$. Gel strength is measured by any convenient method known to those in the art, and typically is measured by a gelometer.

In preparing a gel rehydration electrolyte composition for a typical gel strength test, a portion of water is heated and all non-water ingredients are added. The mixture is stirred at elevated temperature until all non-water ingredients, including the structuring agent, are dissolved. Finally, the remaining water is added and the resulting mixture stirred with continued heating to about 185° F. The mixture is then removed from heat and poured into four 50 ml beakers, each filled to the 40 ml mark. The beakers are placed in a refrigerator at 45° F. and equilibrated for two hours. The beakers are then removed from the refrigerator and gel strength readings are immediately taken using a Stevens 1CM2 gelometer. The measured gel strength is the average of the four readings.

Exemplary structuring agents include but are not limited to agar, alginates, carrageenan, in kappa, iota, or lambda form, cellulose derivatives, exudate gums, gellan gum, gelatin, guar gum, konjac gum, locust bean gum, microcrystalline cellulose, modified starches, pectins, seed gum, and xanthan gum. Preferred structuring agents include but are not limited to gelling agents such as agar, alginate, carrageenan, and pectin. Preferred structuring agents also include but are not limited to thickening agents such as gum arabic, gum tragacanth, tamarind gum, taragum, guar, locust bean gum, and xanthan gum. A most preferred structuring agent is Ticagel® 550, available commercially from TIC Gums Inc., Belcamp, Md. Ticagel® 550 comprises a blend of carrageenan and locust bean gum and produces a preferred composition consistency at room temperature when used in an amount of about 4.5 grams per liter.

Carrageenan is a naturally-occurring hydrocolloid consisting of high molecular weight linear sulfated polysaccharides. It is obtained commercially by extraction from several related species of red algae seaweed and is widely used in the food industry as a stabilizer and gelling agent. The most widely known carrageenans are lambda-, kappa-, iota-, mu-, and nu-carrageenans, described in particular in Janitsyn et al., Handbuch der Kosmetika und Reichstoffe, pages 181–82, Verlag Heidelberg, 1969. The average molecular weight of carrageenans is between 100,000 and 1,000,000.

Locust bean gum or *Ceratonia Siliqua* is cultivated along the Mediterranean shore (Spain, Greece, Italy and North Africa). Locust bean gum is a nonionic polysaccharide comprising straight chain mannan groupings with branching on every second mannose unit by one galactose unit. Locust bean gum is partially soluble in cold water, and completely hydrates when heated.

Either before or after the structuring agent is added, a carbohydrate such as glucose, dextrose, or fructose is added in an amount of about 20–25 grams per liter. Any carbohydrate used in prior art oral rehydration solutions may be used to practice the present invention. Suitable sugars include glucose, fructose and polymers thereof including corn syrup high fructose corn syrup, sucrose, maltodextrin and combinations thereof. Glucose, for example, not only helps to promote sodium and water absorption but provides energy. A preferred carbohydrate source is a mixture of crystalline fructose, sucrose and dextrose. The amount of carbohydrate depends on the selection thereof and is readily determinable by the skilled artisan.

The gel rehydration electrolyte composition of the invention optionally but preferably contains flavoring and/or sweetening agents. While individual perception of flavoring agents and sweetening agents depends on the interrelationship of many factors, flavors and sweeteners may also be perceived separately. Thus, as is well known in the art, flavor and sweetener perception may be both dependent upon each other and independent of each other. For example, when a large amount of flavoring agent is used, a small amount of sweetening agent may be readily perceptible and vice versa. In general, the flavor and sweetener is used in an amount effective to provide a desired taste. Such amounts will vary with the flavor and sweetener selected. The exact range of amounts for each type of sweetener and/or flavoring is known in the art and/or is readily determinable by the skilled artisan.

Flavoring agents useful in preparing gel rehydration electrolyte compositions of the invention include those flavorings known to the skilled artisan, such as flavoring derived from plants, leaves, flowers, fruits, and the like and mixtures thereof. Representative flavor oils include cinnamon oil and oil of wintergreen (methyl salicylate). Useful flavorants include artificial, natural and synthetic fruit flavors such as citrus oils, including lemon, lime, orange, grape and grapefruit, and fruit essences including apple, strawberry, raspberry, cherry, pineapple, tropical and the like, and mixtures thereof. Artificial flavorings are preferred for use in the practice of this invention. Particularly preferred flavors are artificial fruit flavors.

The sweetening agent used may be selected from a wide range of materials including water-soluble sweeteners, water-soluble artificial sweeteners, water-soluble sweeteners derived from naturally occurring water-soluble sweeteners, and mixtures thereof. Without being limited to particular sweeteners, representative categories and examples include:

(a) water-soluble sweetening agents such as monosaccharides, disaccharides and polysaccharides such as monosaccharides, disaccharides and polysaccharides such as xylose, ribulose, glucose (dextrose), mannose, galactose, fructose (levulose), sucrose(table sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydroganated starch hydrolysates and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one2,2-dioxide (Acesulfame-K), the form of sacchrin, and the like; and (c) water-soluble sweeteners derived from naturally occurring water-soluble sweeteners, such as chlorinated derivatives of ordinary sugar (sucrose), known, for example under the produce designation of Sucralose.

Preferred sugar based sweeteners are dextrose, sucrose, and fructose and mixtures thereof. Preferred sugarless sweeteners are sugar alcohols. Preferred sugar alcohols are selected from the group consisting of sorbitol, xylitol, maltitol, mannitol, and mixtures thereof. Particularly preferred sweetening agents include sucrose, dextrose, fructose, sucralose, acesulfame-k, dextrose, saccharine, aspartame, and high fructose corn syrup.

Sugars such as dextrose, sucrose, and fructose were earlier described herein as being preferred carbohydrates due to their ability to facilitate transport and aid absorption of the electrolytes in the gel. However, as just discussed, sugars can provide benefit as water-soluble sweetening agents. When sugars such as dextrose, sucrose, and fructose are present in formulations prepared according to the present invention, such sugars can be serving solely as carbohydrate, solely as sweetening agent, or as both carbohydrate and sweetening agent.

A coloring agent, if desired, can be used in an amount effective to produce the desired color. Coloring agents include pigments such as itanium dioxide. Particularly useful colorants include water-soluble natural food colors and dyes suitable for food, drug and cosmetic applications. These colorants are known as F.D. & C. dyes and lakes. Illustrative nonlimiting examples include the indigoid dye known as F.D. & C. Blue No. 2, which is the disodium salt of 5,5-indigotindisulfonic acid. Similarly, the dye known as F.D.& C. Green No. 1 comprises a triphenyl-methane dye and is the monosodium salt of 4-[4-(N-ethyl-p-sulfoniumbenzylamine)diphenylmethylene]-[1-(N-ethyl-N-p-sulfoniumbenzyl)-delta-2, 5-cycohexadieeneimine]. A full recitation of all F.D.& C. colorants and their corresponding chemical structures may be found in the Kirk-Othmer Encyclopedia of Chemical Technology, 3$^{rd}$ Edition, Volume 6, pages 561–596.

A preferred gel rehydration electrolyte composition of the invention comprises from about 4 to about 5 grams of Ticagel® 550; from about 20 to 30 grams of glucose or dextrose per liter; and about 45 mEq (1022 mg) of Na$^+$, 20 mEq (784 mg) of K$^+$, 40 mEq (1232 mg) of Cl and 30 Meq (1918 mg) citrate ions per liter. This composition provides all electrolytes at levels required by the American Academy of Pediatrics for oral rehydration formulations sold in the United States.

The gel rehydration electrolyte composition may be in the form of a dry solid that upon dissolution with an appropriate amount of water provides the above described gel rehydration electrolyte composition. The gel rehydration electrolyte composition may be packaged in a sealed plastic container that can be refrigerated and subsequently opened so that the gel may be sucked from the container. Alternatively, and preferably, the gel rehydration electrolyte formulation may be packaged, shipped, and consumed at room temperature in containers containing a desired dose, generally about 2–8 ounces, suitable for spoon feeding.

Gel rehydration electrolyte compositions of the invention may also optionally contain various pharmacological agents such as, for example, an antibiotic. If desired, the gel rehydration electrolyte composition may also contain bioavailable minerals, anabolic nutrients, antioxidants, vitamins, analgesics, and/or suspending agents. Examples of anabolic nutrients include vanodyl sulfate, alphaketoglutarate, inosine. Examples of antioxidants include carotenoids, ascorbic acid and salts thereof, tocopherols, reduced glutathione and coenzyme Q10. As referred to herein, bioavailable minerals include inorganic substances, metals, and the like, required in the human diet. Suitable minerals include manganese chromium, calcium, iron, zinc, selenium, copper, iodine, magnesium, phosphorus, and the like such as magnesium oxide, calcium carbonate, ferrous sulfate, ferrous fumarate, zinc chloride, cupric chloride, calcium iodate; and mixtures thereof. Such minerals may be present as amino acid chelates. An amino acid chelate is defined in the food art as a metal ion from a soluble salt with an amino acid or peptide ligand with a mole ratio of one mole of metal to one to three, preferably two, moles of amino acides to form coordinate covalent bonds.

The term vitamin, as used herein, refers to trace organic substances that are required in the diet and include, without limitation, thiamin riboflavin, nicotinic acid, patothenic acid, pyridoxine, biotin, folic acid, vitamin B$_{12}$, lipoic acid, ascorbic acid, vitamin A, vitamin D, vitamin E and vitamin K. Also included with the term vitamin are the coenzymes thereof. Coenzymes are specific chemical forms of vitamins.

Coenzymes include tiamine pyrophosphates (TPP), flavin mononucleotide (FMM), flavin adenine dinucleotide (FAD), nicotinamide adenine dinucleotide (AND), nicotinamide adenine dinucleotide phosphate (NADP) Coenzyme A (CoA) pyridoxal phosphate, biocytin, tetrahydrofolic acid, coenzyme B$_{12}$, lipolysine, 11-cis-retinal, and 1,25-dihydroxycholecalciferol. The term vitamin also includes choline, camitine, and alpha beta, and gamma carotenes.

Analgesics include narcotic and non-narcotic analgesics. Exemplary narcotic analgesics include but are not limited to hydrocodone and acetaminophen. Exemplary non-narcotic analgesics include but are not limited to ibuprofen and ultram.

The gel rehydration electrolyte composition of the present invention may be packaged in numerous advantageous ways. It may be packaged as a dry powder to which water is added. It may be packaged in ready-to-consume individual dosages suitable for spoon feeding. It may also be packaged in a sealed flexible plastic container that can be opened at one end so that the contents may be sucked out.

Preferably, the gel rehydration electrolyte composition is provided as a unit dose packaged in a plastic cup and to be spooned out by consumers.

All documents, e.g., patents, journal articles, and textbooks, cited above or below are hereby incorporated by reference in their entirety.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described therein.

EXAMPLE 1

A gel rehydration electrolyte composition was prepared containing the following ingredients:

| Ingredient | Percent by weight |
| --- | --- |
| Water, flavor and color | 96.185 |
| Dextrose | 2.473 |
| Citric Acid | 0.457 |
| Potassium citrate | 0.152 |
| Potassium sorbate | 0.039 |
| Sodium benzoate | 0.020 |
| Salt | 0.219 |
| Sodium citrate | 0.030 |
| Acesulfame Potassium | 0.075 |
| Ticagel ® 550 | 0.450 |

The gel rehydration electrolyte composition was prepared by heating 32 parts of water and dissolving therewithin the sodium benzoate and potassium sorbate. The remaining non-water ingredients were then added and dissolved. Finally, the remaining water was added and the resulting mixture was cooled. The mixture gelled upon cooling and provided a gel rehydration electrolyte composition suitable for spoon feeding.

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as the invention, the following claims conclude this specification.

What is claimed is:

1. A gel rehydration electrolyte composition comprising:
   (a) from about 80 to about 99 percent by weight water;
   (b) from about 20 to about 60 mEq of sodium per liter of water;
   (c) from about 15 to about 25 mEq of potassium per liter of water;
   (d) from about 25 to about 50 mEq of chloride per liter of water;
   (e) from about 20 to about 50 mEq of citrate per liter of water;
   (f) from about 20 to about 30 grams of carbohydrate per liter of water; and
   (g) from about 2 to about 10 grams of a structuring agent per liter of water, wherein the composition has a gel strength of from about 20 to about 1000 grams per cm$^2$.

2. The gel rehydration electrolyte composition of claim 1, wherein the structuring agent is selected from the group consisting of agar, alginates, carrageenan, cellulose derivatives, exudate gums, gellan gum, gelatin, guar gum, konjac gum, locust bean gum, microcrystalline cellulose, modified starches, pectins, seed gum, and xanthan gum.

3. The gel rehydration electrolyte composition of claim 1, wherein the structuring agent is a combination of carrageenan and locust bean gum.

4. The gel rehydration electrolyte composition of claim 1 comprising 45 mEq of sodium per liter of water; 20 mEq of potassium per liter of water; from about 35 to about 40 mEq of chloride per liter of water; and from about 25 to about 30 mEq of citrate per liter of water.

5. The gel rehydration electrolyte composition of claim 1 comprising about 25 grams of carbohydrate per liter.

6. The gel rehydration electrolyte composition of claim 1 further comprising coloring and flavoring agents.

7. A dry powder which upon the addition of an amount of water provides a composition comprising:
   (a) from about 80 to about 99 percent by weight water;
   (b) from about 20 to about 60 mEq of sodium per liter of water;
   (c) from about 15 to about 25 mEq of potassium per liter of water;
   (d) from about 25 to about 50 mEq of chloride per liter of water;
   (e) from about 20 to about 50 mEq of citrate per liter of water;
   (f) from about 20 to about 30 grams of carbohydrate per liter of water; and
   (g) from about 2 to about 10 grams of a structuring agent per liter of water, wherein the composition has a gel strength of from about 20 to about 1000 grams per cm$^2$.

8. The gel rehydration electrolyte composition of claim 1, wherein the composition is spoonable at room temperature.

9. The gel rehydration electrolyte composition of claim 1, wherein the composition is contained in a sealed flexible plastic container which can be opened so that the gel may be orally administered to a patient.

10. A method of replacing lost electrolytes or preventing loss of electrolytes comprising orally administering to an individual in need thereof a gel rehydration electrolyte composition comprising:
    (a) from about 80 to about 99 percent by weight water;
    (b) from about 20 to about 60 mEq of sodium per liter of water;
    (c) from about 15 to about 25 mEq of potassium per liter of water;
    (d) from about 25 to about 50 mEq of chloride per liter of water;
    (e) from about 20 to about 50 mEq of citrate per liter of water;
    (f) from about 20 to about 30 grams of carbohydrate per liter of water; and
    (g) from about 2 to about 10 grams of a structuring agent per liter of water, wherein the composition has a gel strength of from about 20 to about 1000 grams per cm$^2$.

11. The method of claim 10, wherein the structuring agent is a combination of carrageenan and locust bean gum.

\* \* \* \* \*